(12) United States Patent
Fredriksson

(10) Patent No.: US 9,468,776 B2
(45) Date of Patent: Oct. 18, 2016

(54) METHOD AND A SYSTEM FOR OPTIMIZING A RADIATION TREATMENT PLAN BASED ON A REFERENCE DOSE DISTRIBUTION

(75) Inventor: Albin Fredriksson, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 671 days.

(21) Appl. No.: 13/486,638

(22) Filed: Jun. 1, 2012

(65) Prior Publication Data
US 2013/0324784 A1  Dec. 5, 2013

(51) Int. Cl.
*A61N 5/10* (2006.01)

(52) U.S. Cl.
CPC ............ *A61N 5/1031* (2013.01); *A61N 5/103* (2013.01); *A61N 5/1038* (2013.01)

(58) Field of Classification Search
CPC .. A61N 5/103; A61N 5/1031; A61N 5/1034; A61N 5/1038
USPC ................................................ 600/1; 378/65
See application file for complete search history.

(56) References Cited

U.S. PATENT DOCUMENTS

| | | | |
|---|---|---|---|
| 7,593,505 B2 | 9/2009 | Saracen et al. | |
| 7,693,257 B2 * | 4/2010 | Allison | 378/65 |
| 7,801,270 B2 | 9/2010 | Nord et al. | |
| 8,065,246 B2 * | 11/2011 | Bouchard | 706/19 |
| 2005/0201516 A1 * | 9/2005 | Ruchala et al. | 378/65 |
| 2006/0293583 A1 * | 12/2006 | Saracen et al. | 600/407 |
| 2008/0002811 A1 * | 1/2008 | Allison | 378/65 |
| 2008/0063141 A1 * | 3/2008 | Luan et al. | 378/65 |
| 2008/0152085 A1 * | 6/2008 | Saracen et al. | 378/65 |
| 2010/0020931 A1 * | 1/2010 | Otto et al. | 378/65 |
| 2010/0150309 A1 * | 6/2010 | Nord et al. | 378/65 |
| 2011/0052036 A1 * | 3/2011 | Valdivieso Cacique et al. | 382/132 |
| 2011/0087090 A1 * | 4/2011 | Boernert et al. | 600/411 |
| 2011/0091014 A1 * | 4/2011 | Siljamaki | A61N 5/1031 378/65 |
| 2011/0182409 A1 | 7/2011 | Nord et al. | |
| 2012/0014507 A1 | 1/2012 | Wu et al. | |

OTHER PUBLICATIONS

Kevin L. Moore et al., "Quantitative Metrics for Assessing Plan Quality," Elsevier, Sep. 5, 2011, pp. 62-69.
Kevin L. Moore et al., "Experience-Based Quality Control of Clinical Intensity-Modulated Radiotherapy Planning," Elsevier, 2011, pp. 545-551, vol. 81, No. 2.
Binbin Wu et al., "Patient geometry-driven information retrieval for IMRT treatment plan quality control," Medical Physics, Dec. 2009, pp. 5497-5504, vol. 36, No. 12.

(Continued)

*Primary Examiner* — Phillip A Johnston
*Assistant Examiner* — Sean Luck
(74) *Attorney, Agent, or Firm* — Drinker Biddle & Reath LLP

(57) ABSTRACT

A computer-based method for generating an improved radiation therapy treatment plan for a treatment volume having a target and an organ-at-risk. The method includes a step of accessing an existing radiation therapy treatment plan from a memory of a computer, a dose distribution of the existing radiation therapy treatment plan serving as a reference dose distribution; and performing machine parameter optimization on the existing radiation therapy treatment plan with the computer by pursuing an optimization goal to minimize doses to the organ-at-risk, thereby generating the improved radiation therapy treatment plan.

27 Claims, 15 Drawing Sheets

(56) References Cited

OTHER PUBLICATIONS

Binbin Wu et al., "Data-Driven Approach to Generating Achievable Dose-Volume Histogram Objectives in Intensity-Modulated Radiotherapy Planning," Elsevier, 2010, pp. 1-7.
Waltraud Huyer et al., "A New Exact Penalty Function," Institut für Mathematick, Universität Wien, Wien, Austria, pp. 1-18.
Chuan Wu et al., "Treatment plan modification using voxel-based weighting factors / dose prescription," Physics in Medicine and Biology, 2003, pp. 2479-2491, vol. 48, No. 15.
Pavel Lougovski et al., "Toward Truly Optimal IMRT Dose Distribution: Inverse Planning with Voxel-Specific Penalty," Technology in Cancer Research and Treatment, 2010, pp. 1-24 [629-636], vol. 9, No. 6.
Cristian Cotrutz et al., "IMRT dose shaping with regionally variable penalty scheme," Medical Physics, Apr. 2003, pp. 544-551, vol. 30, No. 4.
Cristian Cotrutz et al., "Using voxel-dependent importance factors for interactive DVH-based dose optimization," Physics in Medicine and Biology, May 2, 2002, pp. 1659-1669, vol. 47, No. 10.
Hans T. Chung et al., "Can all Centers Plan Intensity-Modulated Radiotherapy (IMRT) Effectively? An External Audit of Dosimetric Comparisons Between Three-Dimenstion Conformal Radiotherapy and IMRT for Adjuvant Chemoradiation for Gastric Cancer," Elsevier, Int. J. Radiation Oncology Biol. Phys., 2008, pp. 1167-1174, vol. 71, No. 4.
Jörg Bohsung et al., "IMRT treatment planning—A comparative inter-system and inter-centre planning exercise of the Quasimodo group," Radiotherapy and Oncology, 2005, pp. 354-361, vol. 76.
Thomas Bortfeld et al., "Decomposition of pencil beam kernels for fast dose calculations in three-dimensional treatment planning," Medical Physics, Mar./Apr. 1993, pp. 311-318, vol. 20, No. 2.
Anders Ahnesjö, "Collapsed cone convolution of radiant energy for photon dose calculation in heterogeneous media," Medical Physics, Jul./Aug. 1989, pp. 577-592, vol. 16, No. 4.
ICRU Report 62, Prescribing, Recording and Reporting Photon Beam Therapy (Supplement to ICRU Report 50), International Commission on Radiation Units and Measurements, Nov. 1, 1999, Bethesda, MD (USA).
Ph.D. Thesis of Johan Löf, "Development of a general framework for optimization of radiation therapy," Department of Medical Radiation Physics of Stockholm University, 2000.
Breedveld et al., "A novel approach to multi-criteria inverse planning for IMRT," IOP publishing, Physics in Medicine and Biology, vol. 52, pp. 6339-6353, 2007.
Fiege et al., "A novel evolutionaty optimization approach to multiobjective IMRT planning," Medical Physics, vol. 38, No. 9, pp. 5217-5229, 2011.
International Preliminary Report on Patentability and Written Opinion mailed Dec. 11, 2014 in International Application No. PCT/IB2013/001101, 6 pages.

* cited by examiner

METHOD AND A SYSTEM FOR OPTIMIZING A RADIATION TREATMENT PLAN BASED ON A REFERENCE DOSE DISTRIBUTION

TECHNICAL FIELD

This invention relates to the field of radiation treatment, in particular the optimization of a radiation therapy treatment plan based on an existing radiation therapy treatment plan.

BACKGROUND

In the field of radiation therapy treatment planning, treatment planners usually generate an intensity-modulated radiation therapy (IMRT) treatment plan after having knowledge of the to-be-treated target volume in a patient's body, for example by using a computer tomography (CT) scanner. The target volume is usually an organ in a patient's body that is affected by a tumor, for example a cancer. However, studies have shown that the quality of the treatment plans is closely linked to the experience of the treatment planner. This suggests that many treatment plans have room for improvement, especially if prepared by a less experienced planner. Moreover, the use of inadequate planning methods, early termination of the optimization process, or measuring plan quality with improper or blunt fitness functions often lead to inadequate radiation therapy treatment plans. Examples of the latter fitness functions are the semideviation penalties, which penalize volumetric units with doses above or below some threshold, often utilized in treatment plan optimization: When just volumetric units that receive doses higher than a prescribed dose level are penalized, the only incentive for the optimization algorithm is to reduce the dose to that very level, even though lower doses may well be attainable without any sacrifice of other treatment goals.

As an example, the publication "Patient geometry-driven information retrieval for IMRT treatment plan quality control," from B. Wu, F. Ricchetti, G. Sanguineti, M. Kazhdan, P. Simari, M. Chuang, R. Taylor, R. Jacques, and T. McNutt, of Medical Physics, Vol. 36(12), pages 5497-5505, 2009, presents a method for quality control of treatment plans. In this method, when a new plan has been prepared, its patient geometry is matched against those in a database of previous plans. Structures for which the doses in the new plan are worse than the doses in previous plans with similar geometries are flagged as being potential subjects for improvements. The plans are then reoptimized with stricter dose requirements for the flagged structures.

The methods proposed by the publications "Using voxel-dependent importance factors for interactive DVH-based dose optimization," from C. Cotrutz and L. Xing, Physics in Medicine and Biology, Vol. 47(10). Pages 1659-1669, 2002, and "IMRT dose shaping with regionally variable penalty scheme," also from C. Cotrutz and L. Xing, Medical Physics, Vol. 30(4), pages 544-551, 2003 suggest to use voxel-specific weighting factors to convey the importance of different volumes in the patient geometry to the optimization algorithm for dose-volume histograms (DVH). They perform optimizations iteratively to carefully balance the trade-offs between planning criteria. The publication "Treatment plan modification using voxel-based weighting factors/dose prescription," Physics in Medicine and Biology, Vol. 48(15), pp. 2479, 2003 from C. Wu, G. H. Olivera, R. Jeraj, H. Keller, and T. R. Mackie also suggests to perform optimizations iteratively, in which they update the weighting factors or the prescribed doses to each voxel. They find that the two types of updates are equivalent under certain conditions.

Similarly, the publication "Toward truly optimal IMRT dose distribution: inverse planning with voxel-specific penalty" from P. Lougovski, J. LeNoach, L. Zhu, Y. Ma, Y. Censor, and L. Xing, Technology in Cancer Research and Treatment, Vol. 9(6), pages 629-636, 2010, proposes to construct a scheme in which the prescribed dose levels are iteratively updated for voxels not satisfying the ideal dose prescriptions of uniform target dose and zero dose to healthy tissues. In addition, the method described by the Ph.D. Thesis of Johan L of, entitled "Development of a general framework for optimization of radiation therapy," of the Department of Medical Radiation Physics of Stockholm University, 2000, the optimization of the complication free tumor control probability is followed by a minimization of the integral dose under the constraint that the complication free tumor control probability can only be marginally worse than in the first optimization.

Despite all the above discussed strategies, quality control, and optimization methods, there is still a strong need for better radiation therapy treatment plans that are generated by using novel methods and strategies that allow to improve or optimize upon existing radiation treatment plans.

SUMMARY OF THE INVENTION

According to one aspect of the present invention a computer-based method for generating an improved radiation therapy treatment plan for a treatment volume having a target and an organ-at-risk is provided. Preferably, the method includes a step of accessing an existing radiation therapy treatment plan for the treatment volume from a memory of a computer, a dose distribution of the existing radiation therapy treatment plan serving as a reference dose distribution. In addition, the method preferably includes a step of performing machine parameter optimization on the existing radiation therapy treatment plan with the computer by pursuing an optimization goal to minimize doses to the organ-at-risk, thereby generating the improved radiation therapy treatment plan.

According to another aspect of the present invention, a computer system for generating an improved radiation therapy treatment plan for a treatment volume having a target and an organ-at-risk is provided. Preferably the system includes a storage device for storing an existing radiation therapy treatment plan for the treatment volume, a dose distribution of the existing radiation therapy treatment plan serving as a reference dose distribution. In addition, the system preferably includes a hardware processor for performing machine parameter optimization on the existing radiation therapy treatment plan by pursuing an optimization goal to minimize doses to the organ-at-risk, thereby generating the improved radiation therapy treatment plan.

According to yet another aspect of the present invention, a non-transitory computer readable medium is provided, having computer instructions recorded thereon, the computer instructions configured to perform a method for generating an improved radiation therapy treatment plan for a treatment volume having a target and an organ-at-risk when executed on a computer. Preferably, the method includes a step of accessing an existing radiation therapy treatment plan for the treatment volume from a memory of a computer, a dose distribution of the existing radiation therapy treatment plan serving as a reference dose distribution. In addition, the method further preferably includes a step of performing machine parameter optimization on the existing radiation therapy treatment plan with the computer by pursuing an optimization goal to minimize doses to the organ-at-risk, thereby generating the improved radiation therapy treatment plan.

The present invention allows pursuing an optimization goal by an algorithm that can exploit a possible leeway that was left by other treatment planning methods. Basically, the dose distribution of a previous, existing radiation therapy treatment plan is taken and an optimization is performed towards a new plan in which it is possible that either the dose to the voxels or the DVH of the regions of interest (ROI) is at least as good as in the previous plan. The result of the optimization method is a radiation treatment plan that can be delivered to a patient. With this method, a goal is to automatically create better radiation therapy treatment plans by a computer-based method and find the criteria of an existing radiation therapy treatment plans that can be more strictly enforced. The present invention can be used in a clinical setting as well as in the education of treatment planners so that a radiologist can determine where and how the existing plans could be further improved.

The summary of this invention is neither intended nor should it be construed as being representative of the full extent and scope of the present invention, which additional aspects will become more readily apparent from the detailed description, particularly when taken together with the appended drawings.

BRIEF DESCRIPTION OF THE DRAWINGS

These and other features, aspects and advantages of the present invention will become better understood with regard to the following description, appended claims, and accompanying drawings where:

Herein, identical reference numerals are used, where possible, to designate identical elements that are common to the figures. Also, the images in the drawings are simplified for illustrative purposes and are not necessarily depicted to scale.

DETAILED DESCRIPTION

Figure 1:
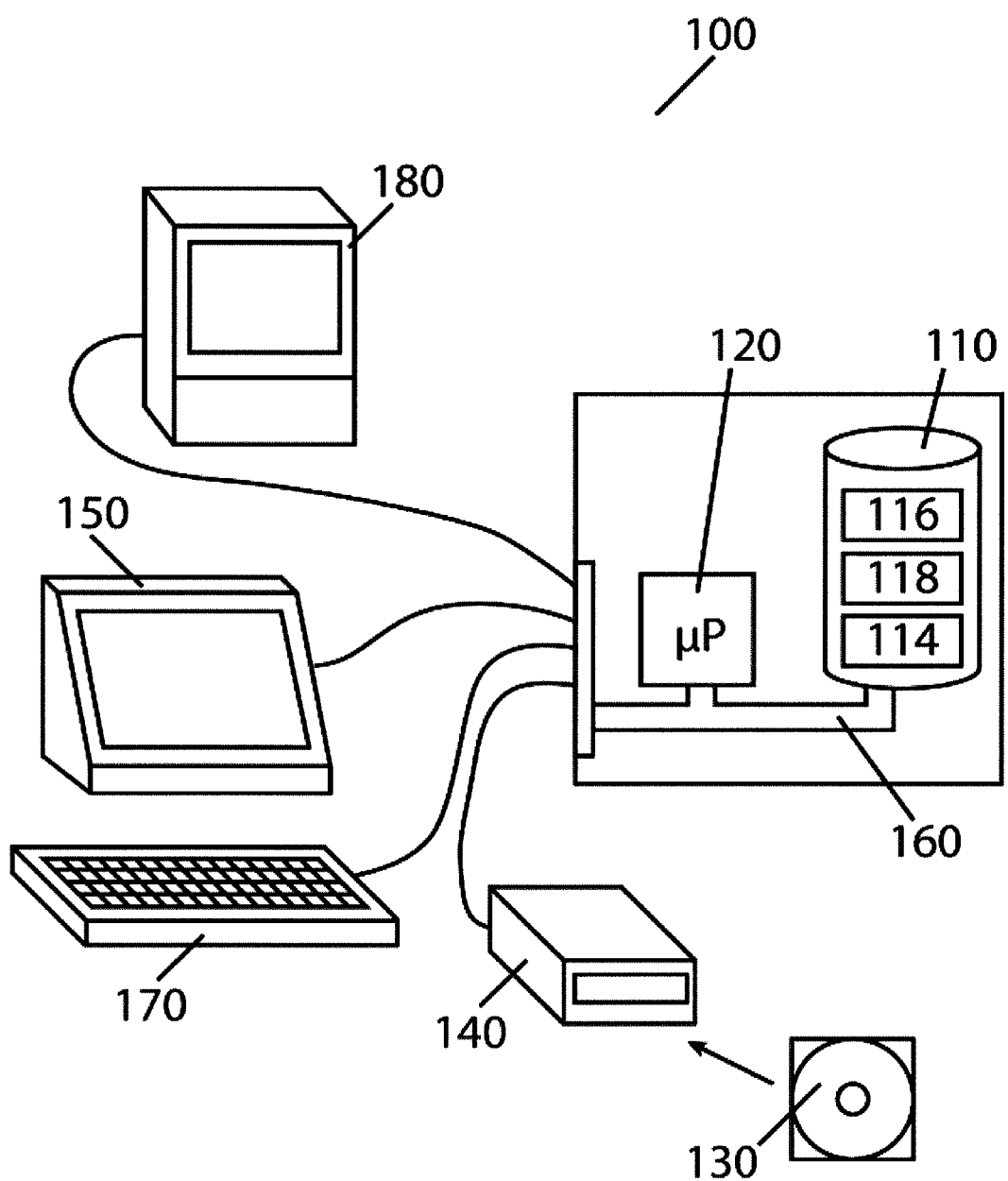
FIG. 1 schematically shows a computer-based system for performing a method to optimize an existing radiation therapy treatment plan.

FIG. 1 shows a simplified schematic representation of a computer-based system 100 for performing an optimization method to improve an existing radiation therapy treatment plan 114, according to the present invention. The computer-based system 100 includes a memory or database 110 having an existing radiation therapy treatment plan 114 stored thereon, and a computer program 116 for optimizing or improving the existing radiation therapy treatment plan 114 to generate an improver radiation therapy treatment plan 118. Memory 110 can be any volatile or non-volatile memory device such as a flash drive, hard drive, optical drive, dynamic random access memory (DRAM), static random access memory (SRAM), and any other suitable device for storing information and later information retrieval and use for data processing. Also, the system 100 includes one or more hardware processors 120 for performing data processing and able to access the memory 110. The hardware processor 120 can be made of one or more central processing unit (CPU), digital signal processor (DSP), reduced instruction set computer (RISC), application specific integrated circuit (ASIC), complex programmable logic device (CPLD), field-programmable gate arrays (FPGA), parallel processor systems, or a combination of these different hardware processor types.

The computer program 116 is made of computer-readable instructions that can be transferred to hardware processor 120, and can be executed by hardware processor 120. When executed on the hardware processor 120, the computer-readable instructions will perform a method for optimizing or improving the existing radiation therapy treatment plan 114. Results of the processing that is performed by the hardware processor 120 when executing the computer program 116 can be stored in memory 110, for example the improved radiation therapy treatment plan 118, and associated data. Hardware processor 120 can also access the memory 110 via direct memory access (DMA), and can also use a cache memory for storing temporary processing results. The computer program 116 can also be stored on a non-transitory computer readable medium 130, for example a universal serial bus (USB) flash drive, optical data carriers such as CD-ROM, DVD-ROM, and Blu-Ray disk, floppy disk, swappable hardware drives, USB external hard drive (HDD), or any other portable information storage device, so that the computer program 116 can be transferred to different computing systems, and also loaded to the memory 110 of system 100. This can be done by connecting the computer readable medium 130 via a data reader/writer 140 to system 100, for example an optical drive, USB interface, etc.

Moreover, the system 100 also includes a display unit 150 that also has a display driver that allows to visualize the results of the data processing, for example to visualize three-dimensional (3D) representations of a target volume of a patient containing, for example, a tumor or cancer cell, and healthy organs-at-risk for which dose delivery has to be prevented, 3D contour data, or two-dimensional (2D) slice representations for various intersection directions, etc. For example, a 3D computer reproduction of a CT scan can be displayed. Also, display unit 150 can display DVH that summarize 3D dose distribution by using a graphical 2D format. For example, the display unit 150 is configured to show comparative DVH diagrams for volumes of the patient showing a dose contribution of the existing radiation therapy treatment plan 114, and for the same volumes of the optimized or improved radiation therapy treatment plan, so that the improvement can be visually compared. Also, it is possible that the display unit 150 is equipped with a touch screen functionality and can display a graphical user interface to operate system 100.

In addition, computer system 100 has a system bus 160 that connects the hardware processor 120, memory 110, data reader 140, touch screen, and various other data input-output interfaces and peripheral device that are not shown. For example, the computer system 100 can be connected to a keyboard 170 for data input by a user, and may be connected to an external radiation treatment planning device 180 that has created the existing radiation therapy treatment plan, for example a powerful special-purpose computer. Also, the system 100 may be connected to a CT scanner that is not shown. For example, external device 180 that created the existing radiation therapy treatment plan 114 may be able to develop a dose calculation algorithm that is coded into software, has access to radiation data on prescribed dose distribution, and machine calibration data, and patient-specific information on the target volume of and organs-at-risk of the patient. This external device 180 can then deliver the existing radiation therapy treatment plan 114 to computer system 100 for improvement and optimization. However, it is also possible that computer program 116 is run on the external device itself, thereby not only generating the existing radiation therapy treatment plan 114, but also generating the improved radiation therapy treatment plan 118.

Figure 2:
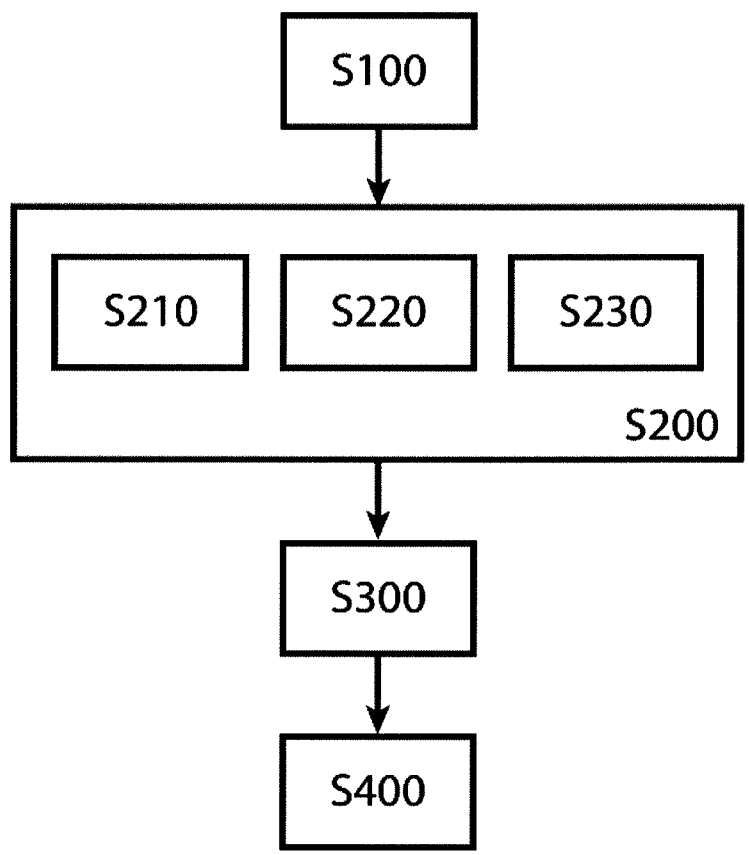
FIG. 2 shows a diagram representing the steps of a computer-based method for optimizing an existing radiation therapy treatment plan.

FIG. 2 shows a simplified schematic representation of a method to improve an existing radiation therapy treatment plan 114 according to the present invention. First, the method accesses an existing radiation therapy treatment plan 114, for example for a specific treatment volume of a patient's body, from memory 110 of system 100. Given a dose distribution $d^{ref}$ of an existing radiation therapy treatment plan 114, an optimization step S200 is performed aiming at minimizing the dose under the constraints that no ROI be worse off than under $d^{ref}$. Thereby, a dose distribution curve, DVH curves, or a volumetric 3D representation of the dose distribution can be used as a measure. The ROIs of the existing radiation therapy treatment plan 114 are indexed by the set R, which is partitioned into set O for the OARs, and T for the target volumes, with O including the external ROI. In one variant, the optimization goal of the method is to improve upon the existing radiation therapy treatment plan 114 by minimizing the penalty of a criterion, while other criteria are enforced to be no worse than in the existing plan 114. More specifically, the method can attempt to ascertain that the sum of mean doses to the OARs is minimized under the constraint that no ROI can receive a dose that is worse than in $d^{ref}$. Also, the method can aim to minimize a sum of other dose-based functions that are administered to the OARs, such as the sum of doses raised to a power p, the sum of doses above a threshold, the maximum dose, etc. The prescribed doses for the target volumes r that are part of T (r∈T) are given as $\hat{d}_r$, but could also be specified for each individual volumetric unit.

The method to improve the existing radiation therapy treatment plan 114 therefore performs an optimization based on the dose distribution $d^{ref}$ of the existing plan 114 serving as a reference with a main optimization goal in step S200 of minimizing the sum of the doses to the OARs, preferably minimizing the sum of the mean doses to the OARs. By this method, voxels or DVH of portions of the improved plan 118 can be at least as good as the reference plan. More preferably, the method aims to ascertain that each voxel or each DVH of portions of the improved plan 118 at least as good as the reference plan. At the same time, the prescribed doses $\hat{d}_r$ to the target ROI are also preserved. A voxel is defined as a volumetric element of the treatment volume, representing a value on a regular grid in three dimensional space in Cartesian coordinates, and is hereinafter indexed with the letter i. Preferably, the size of the voxel can be between $0.01^3$ cm$^3$ and $2^3$ cm$^3$ depending on the required granularity of the optimization method, and the processing time. It is also possible that volumetric units other than voxels be, for example by using volumetric units that are based on other polyhedra, a spherical coordinate system or cylindrical coordinate system.

Figure 3:
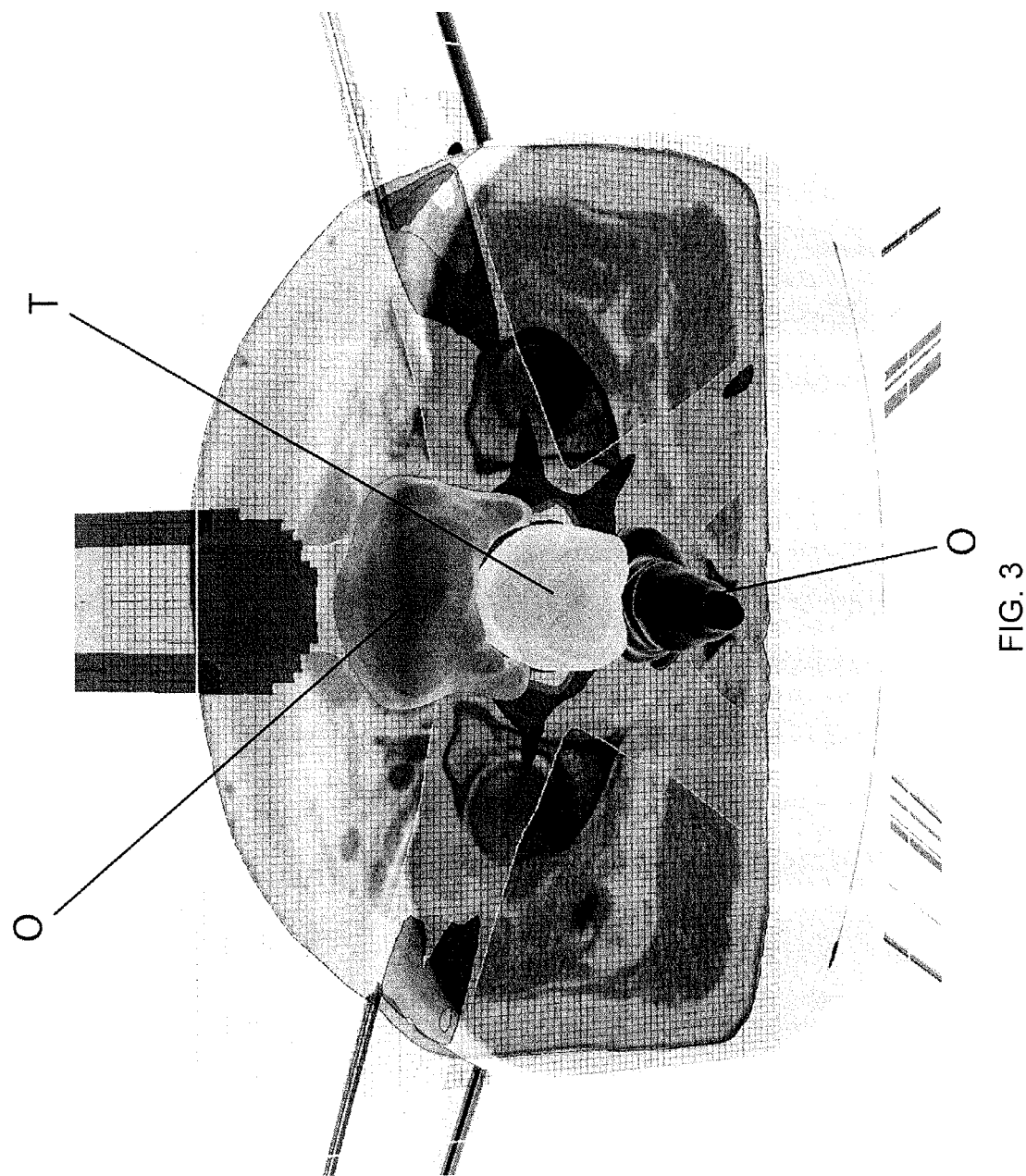
FIG. 3 shows a three dimensional image with a portion of a patient and a target volume that is irradiated by radiation beams.

FIG. 3 represents a 3D representation of a CT image of a target volume T, for example a prostate that is affected by cancer in a lower body torso. In addition, five beams are represented that enter into the body from five different angles of a IMRT radiation treatment apparatus. Other radiation treatment plans for different types of radiation therapy apparatuses, such as Three-Dimensional Conformal Radiation Therapy (3DCRT), Volumetric Modulated Arc Therapy (VMAT), or Intensity-Modulated Proton Therapy (IMPT) treatment plans can also be optimized by the method. Also, OARs O are shown that have to be exposed to as little radiation as possible, for example the rectum. Moreover, a grid is represented in the background, each element of the grid representing a side wall of voxel of cubic shape that will be used for the optimization method. In an ideal world, the OARs O would not be irradiated at all, while the target volume T would be homogenously irradiated with a prescribed dose $\hat{d}_r$. However, since the radiation has to arrive to the target volume T from the outside of the patient, this goal cannot be fully reached, but can be approached by aiming different optimization goals.

The optimization goal in step S200 of minimizing the sum of the mean doses to the OARs can be pursued by optimizing under different constraints. The step S200 is hereinafter described as optimizing voxels and the associated radiation dose $d_i(x)$, but as described later, it is also possible that the same optimization goals are optimized on volumes based on the DVH $D_r(v; x)$ that is associated to each portion or volume, and the reference DVH $D_r^{ref}(v)$ of the existing radiation therapy treatment plan, as described later. A first constraint to pursue in the optimization method is to aim that voxels of an OAR cannot receive higher dose than in the reference dose distribution $d^{ref}$, in a step S210, more preferably all the voxels cannot receive a higher dose. In addition, a second constraint to pursue in the optimization method is to aim that no voxel of any target can receive a lower dose than the reference dose $D^{ref}$ of each corresponding voxel, or do not receive a dose that is lower than prescribed dose $\hat{d}_r$ to the target, in a step S220. Moreover, a third constraint to pursue in the optimization method is to aim that no voxel of any target can receive a higher dose than the reference dose $d^{ref}$ in the corresponding voxel, or do not receive a dose that is higher than the prescribed dose $\hat{d}_r$ to the target, in a step S230. These steps S210, S220 and S230 can be performed in parallel or sequentially and preserve the overall optimization goal of step S200 of minimizing the sum of the mean doses to the OARs. An optimization algorithm can be used to pursue to goal of minimizing the OAR doses while enforcing that the constraints of steps S210, S220 and S230 are fulfilled.

The constraints given by steps S220 and S230 thus enforce the dose of each voxel i of all the voxels $V_r$ (i∈$V_r$) for each target ROI r of all target volumes T (r∈T) to lie within an interval [min{$d_i^{ref}, \hat{d}_r$}, max{$d_i^{ref}, \hat{d}_r$}]. It is also possible that the optimization functions that are expressed by steps S200, S210, S220, S230 could also be designed to improve or optimize on other goals, for example to reduce the integral dose, to increase the target coverage or the sparing of a subset of the OARs, to reduce the number of monitor units, to reduce the delivery time, or a combination of such goals. When there is no room for improvement on the integral dose, minimizing the OAR doses are often beneficial, since such minimization can lead to redistributions of the dose, decreasing the irradiation of the OARs to further reduce their dose concentration.

With the prescribed doses for the target ROI is denoted as $\hat{d}_r$, is desired for each target ROI r that is part of the set T (r∈T), such an optimization problem can be expressed by the following equations:

$$\min_{x \in X} \sum_{r \in O} \sum_{i \in V_r} \Delta v_i^r d_i(x) \qquad (1)$$

subject to:

$$\sum_{i \in V_r} \Delta v_i^r \left(d_i(x) - d_i^{ref}\right)_+ \leq 0, \quad r \in O \qquad (2)$$

$$\sum_{i \in V_r} \Delta v_i^r \left(\min\{d_i^{ref}, \hat{d}_r\} - d_i(x)\right)_+ \leq 0, \quad r \in T \qquad (3)$$

$$\sum_{i \in V_r} \Delta v_i^r \left(d_i(x) - \max\{d_i^{ref}, \hat{d}_r\}\right)_+ \leq 0, \quad r \in T \qquad (4)$$

where $V_r$ indexes all the voxels of one ROI r that is part of the set of OAR R, and $d_i(x)$ is the dose to voxel i as a function of the optimization variables x, that can include machine parameters such as bixel weights, spot weights, multi-leaf collimator leaf positions, jaw positions, segment weights, monitor units, collimator angles, couch angles, gantry angles, wedge angles, arc delivery times, etc. Moreover, x is part of the set X of feasible variables, in other words feasible machine parameters. In addition, $\Delta v_i^r$ is the relative volume of voxel i that lies within ROI r, such that the following equation is satisfied:

$$\sum_{i \in V_r} \Delta v_i^r = 1 \qquad (5)$$

Furthermore, the shorthand $y_+$ denotes the positive part $\max\{y, 0\}$ of y. To avoid increasing plan complexity, constraints on the monitor units and, for VMAT, the delivery time could additionally be enforced.

In theory, there is no need to aggregate the constraints per ROI: satisfying the aggregate constraint $$\sum_{i \in V_r} \Delta v_i^r \left(d_i(x) - d_i^{ref}\right)_+ \leq 0 \qquad (6)$$

is equivalent to satisfying constraints $d_i(x) \leq d_i^{ref}$ for each voxel i that is part of $V_r$ (i∈$V_r$) in each OAR r that is part of O (r∈O), and similarly for the target constraints expressed in Equations (3) and (4). In general, nonlinear optimization solvers are necessary for this type of problem, because of the nonlinear relationship between optimization variables of the machine parameters, such as bixel weights, spot weights, multi-leaf collimator leaf positions, segment weights, monitor units, collimator angles, jaw positions, couch angles, gantry angles, wedge angles, arc delivery times, etc. and dose, unless pencil beam scanning, fluence map optimization or segment weight optimization is performed, in which case linear programming could be used. Therefore, the large number of voxels may make such individual constraints for each voxel too time-consuming to be practical. For many nonlinear programming solvers, it is also possible to square the optimization goals as expressed in Equations (1)-(4) or their summands, in order to introduce curvature into the optimization problem. For Equations (1)-(4), the squaring the summands changes the optimal solution of the optimization problem, namely to one that minimizes the sum of the mean squared doses, which will emphasize the importance of reducing high doses. If instead the whole sum of the objective is squared and at the same time either the summands or the whole sums of the constraints are squared, the optimal solution remains the same as the one to Equations (1)-(4).

Figure 4:
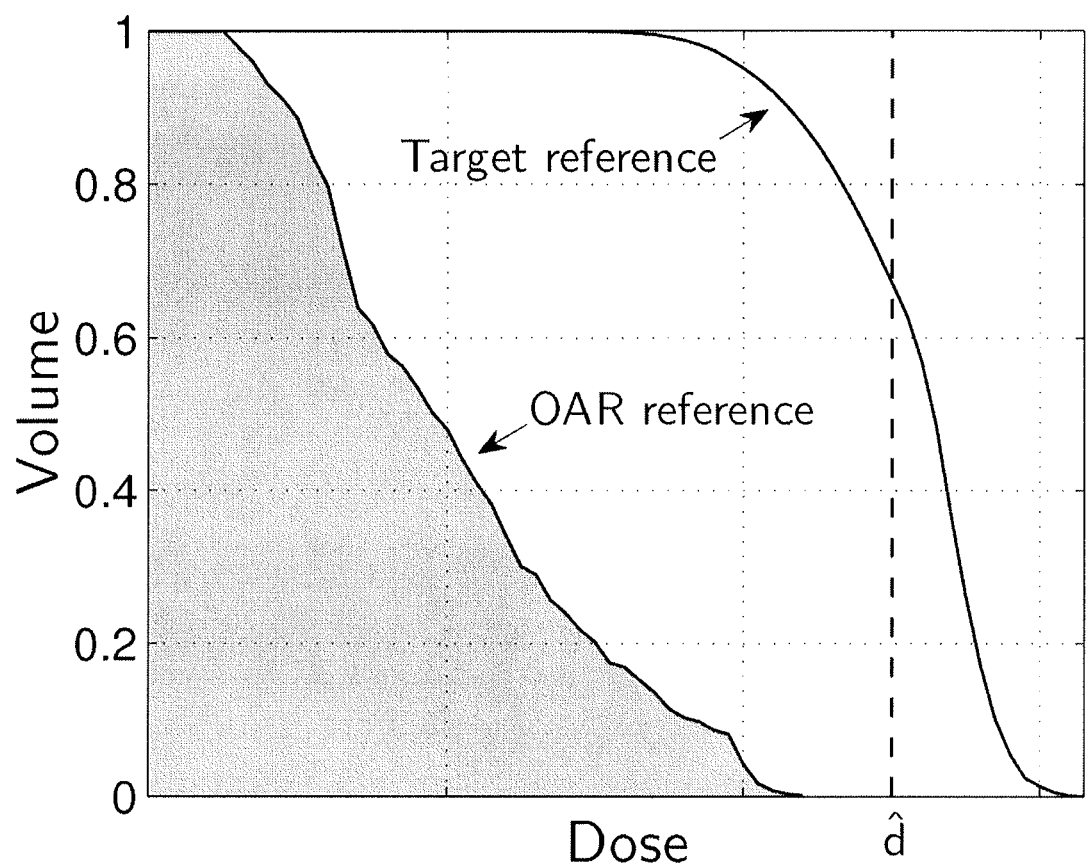
FIG. 4 shows a DVH representation for an Organ-at-Risk (OAR) and a target volume together with a prescribed dose level.

As shown in FIG. 4, in a variant of the present invention, instead of enforcing that each voxel $d_i(x)$ be no worse off than the associated reference dose distribution $d_i^{ref}$, it is also possible to perform an optimization that optimizes volumes based on the DVH $D_r(v; x)$ that is associated to each volume, and the reference DVH $D_r^{ref}(v)$ of the corresponding volume of the existing radiation therapy treatment plan 114. In some situations, the voxel-based optimization method can be an overly conservative optimization goal since often the DVHs of individual volumes or organs may be of more interest than the individual voxels. One can thus modify the constraints as not to penalize the deviation of each voxel $d_i(x)$ from the reference dose $d_i^{ref}$, but the deviation of each DVH $D_r(v; x)$ from the corresponding DVH of the reference dose distribution $D_r^{ref}(v)$.

The DVH constraints depend on the functions $D_r(v; x)$ and $D_r^{ref}(v)$, which parameterize respectively the planning DVH, given the machine parameters x that are part of X (x∈X), and the reference DVHs as functions of the volume v∈(0, 1]. The function $D_r(v; x)$ is defined as the highest dose level d in the planning dose distribution such that a fraction v of the volume of ROI r that is part of R (r∈R) receives a dose greater than or equal to d. The function $D_r^{ref}(v)$ is defined analogously, but for the reference dose distribution instead of the planning dose distribution. Instead of the maximum dose constraint that is given in Equation (2), a maximum reference DVH constraint is now used, which does not allow any part of the DVH $D_r(v)$ to exceed the reference DVH $D_r^{ref}(v)$. Instead of the minimum target dose constraint that is given in Equation (3), a minimum target reference DVH constraint is now used, to ascertain that no volume of any target can receive a lower dose than the reference DVH $D_r^{ref}$ of each corresponding volume, or do not receive a dose that is lower than prescribed dose $\hat{d}_r$. Moreover, instead of the maximum target dose constraint that is given in Equation (4), a maximum target reference DVH constraint is now used, to ascertain that no volume of any target can receive a higher dose than the reference DVH $D_r^{ref}$ of the corresponding volume, or do not receive a dose that is higher than the prescribed dose $\hat{d}_r$.

FIG. 3 depicts the admissible DVH curve diagram for an OAR from the set O in dark gray color, and a target ROI from the set T in light gray color under a given reference dose distribution $d^{ref}$. Also, the prescribed dose $\hat{d}_r$ is indicated as a dotted line. Therefore, the DVH-based optimization problem can be expressed by the following equations:

$$\min_{x \in X} \sum_{r \in O} \sum_{i \in V_r} \Delta v_i^r d_i(x) \qquad (7)$$

subject to:

$$\int_0^1 (D_r(v; x) - D_r^{ref}(v))_+ dv \leq 0, \quad r \in O \qquad (8)$$

$$\int_0^1 \left(\min\{D_r^{ref}(v), \hat{a}_r\} - D_r(v;x)\right)_+ dv \leq 0, r \in T \quad (9)$$

$$\int_0^1 \left(D_r(v;x) - \max\{D_i^{ref}(v), \hat{a}_r\}\right)_+ dv \leq 0, r \in T \quad (10)$$

As an alternative to the voxel-based optimization functions expressed in Equations (1)-(4) and reference DVH-based optimization functions expressed in Equations (7)-(10), is to enforce the reference dose distribution in voxel clusters, grouping several neighboring voxels into a cluster. The mean doses of the entire clusters of voxels are then constrained to be no worse than the corresponding mean doses of the corresponding reference dose distribution. This variant is still less conservative than the voxel-specific requirements but preserves convexity.

The above described methods to improve the existing radiation therapy treatment plan is not primarily intended to better solve the main treatment conflicts, but is intended to be applied to any radiation therapy treatment plan that may have been generated by any planning method, in order to improve thereupon. Usually, the method is performed only once without user input, and does not require multiple optimization rounds, nor does it require an entire database of previously optimized treatment plans.

Another aspect of the present invention is the regularization of the positive part functions or maximum functions. A difficulty with optimization functions like the optimization functions in Equations (1)-(4) and (7)-(10) is that the gradients vanish for feasible solutions. For example, for all points satisfying the constraints, all the positive part functions evaluate to zero, which implies that the gradients are zero in the interior of the feasible region, that would likely be the optimum solution. Moreover, since positive part functions have discontinuous derivatives at zero, the gradients of the constraints have discontinuities.

Figure 5:
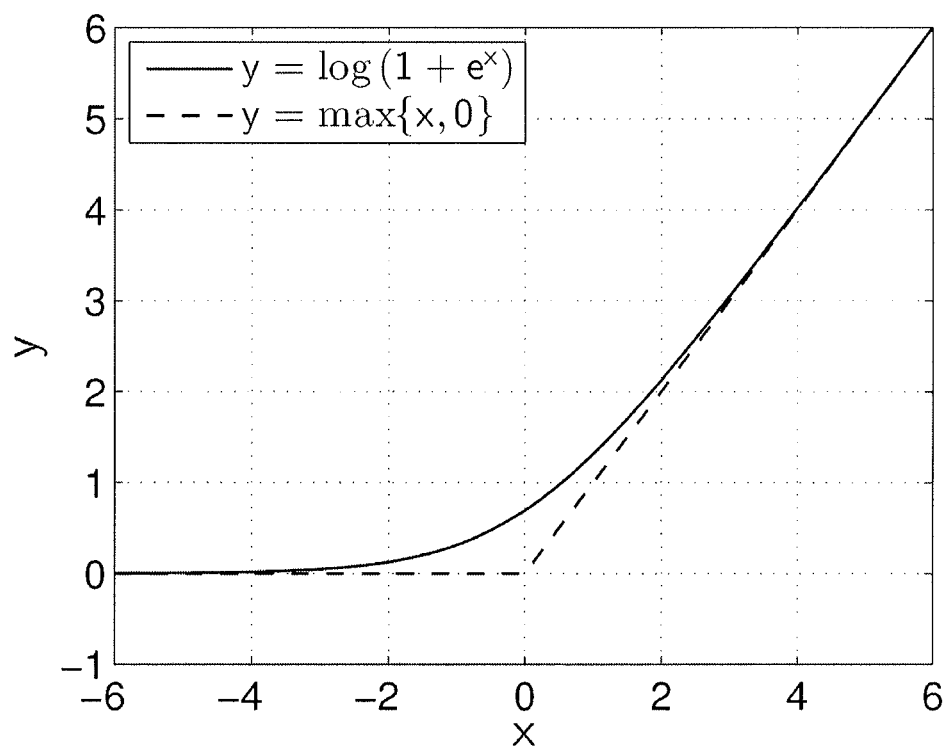
FIG. 5 shows a log-sum-exp function with a solid line, and the maximum function or positive part function with a dashed line.
Figure 6A:
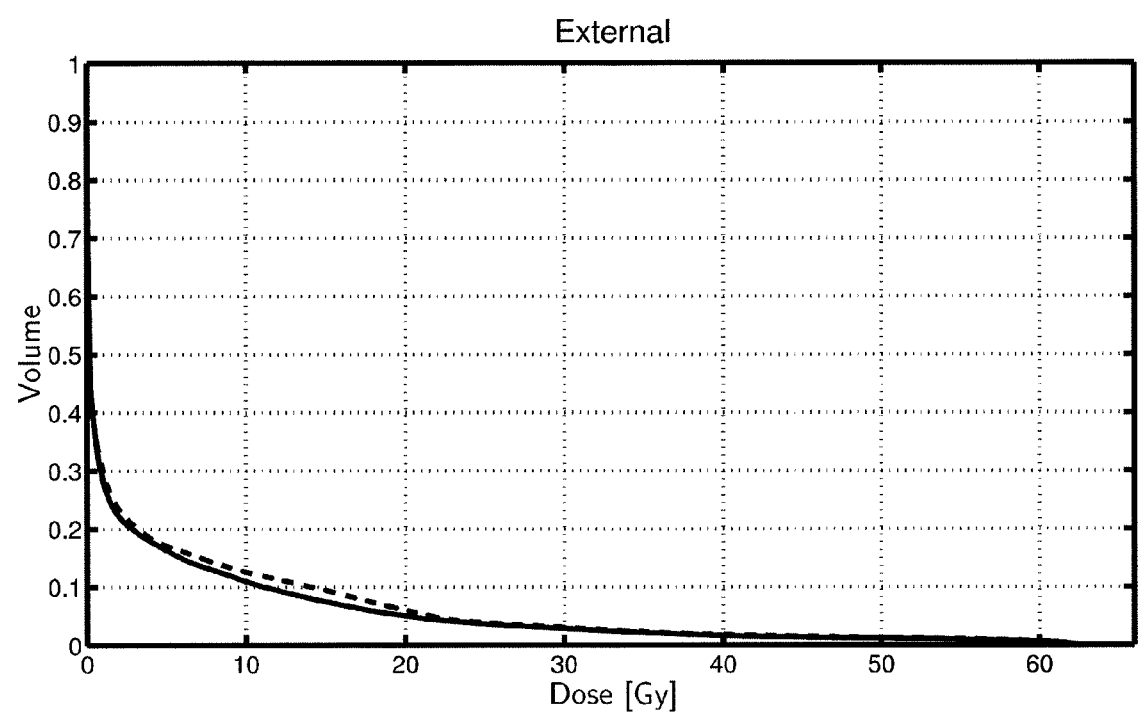
FIGS. 6A-6J show DVHs of different volumes for the existing radiation therapy treatment plan and the DVHs of the same volumes for the optimized radiation therapy treatment plan after performing the method.
Figure 6B:
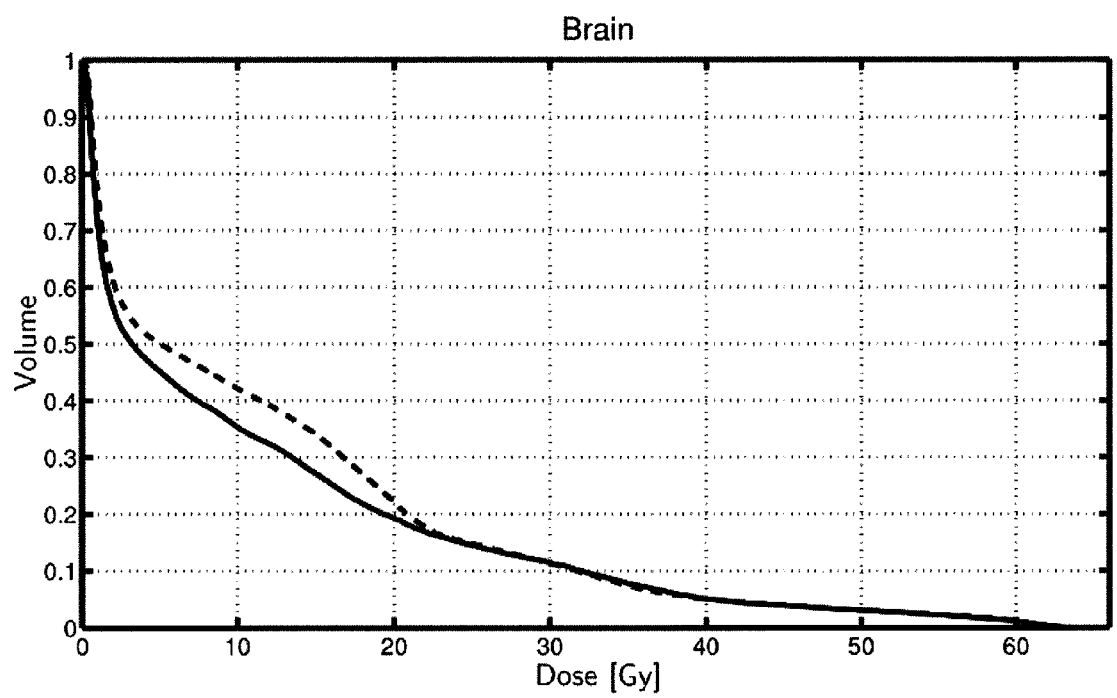
Figure 6C:
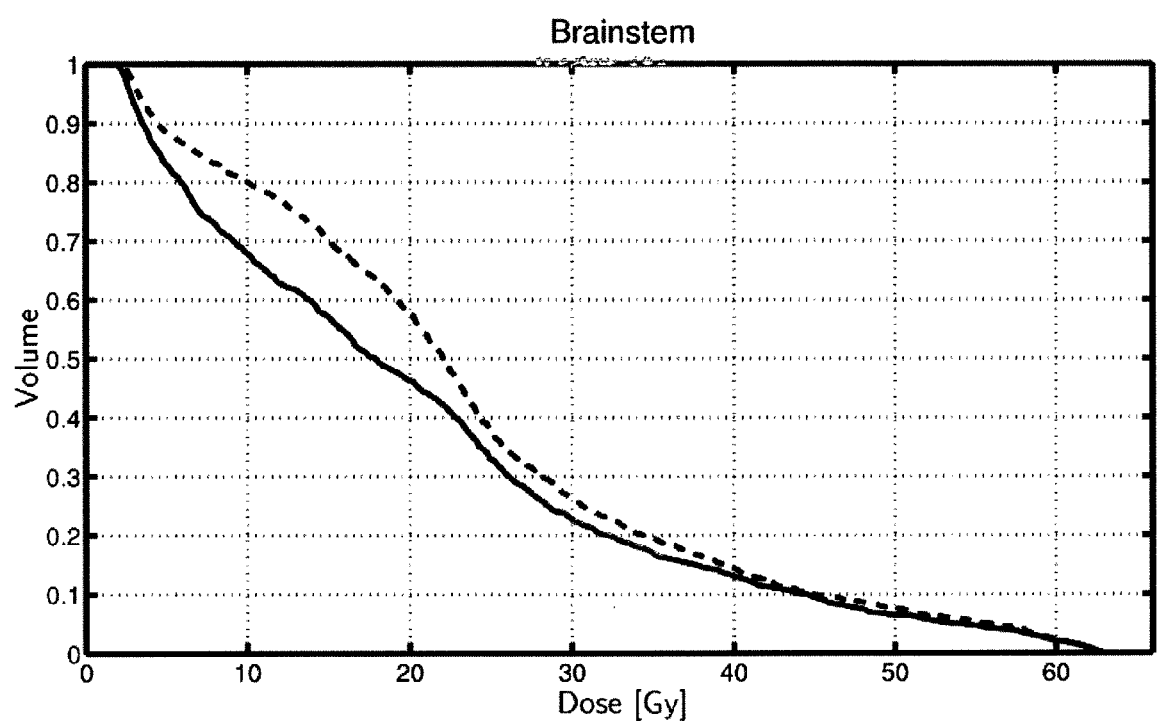
Figure 6D:
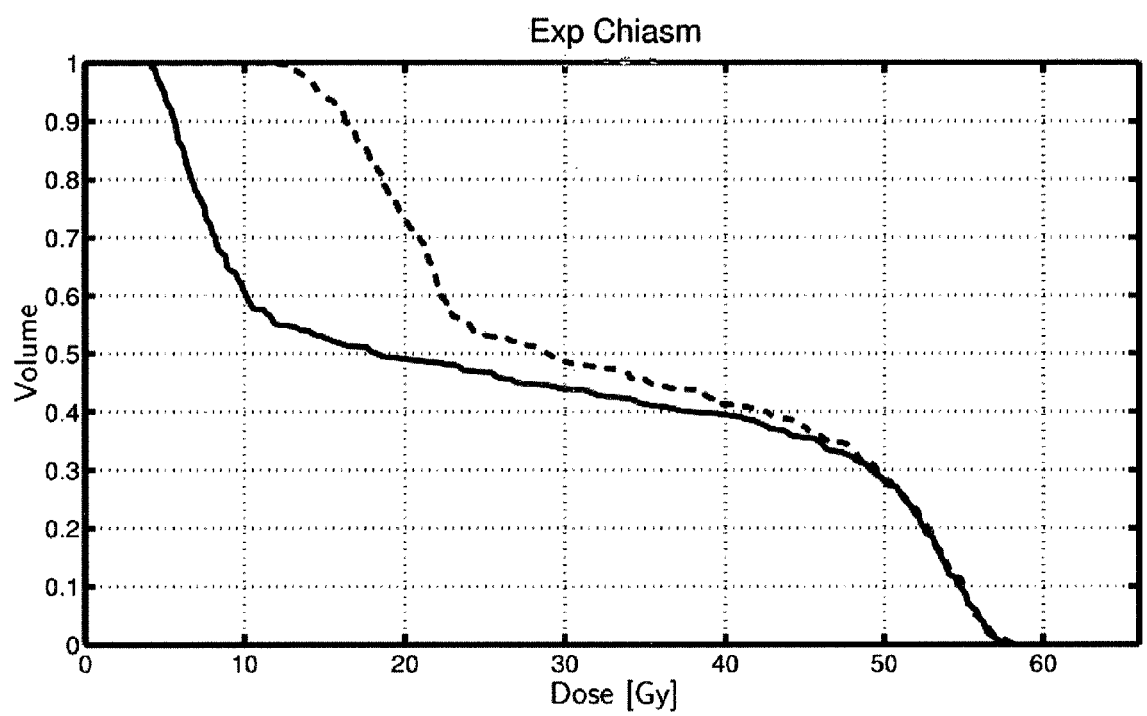
Figure 6E:
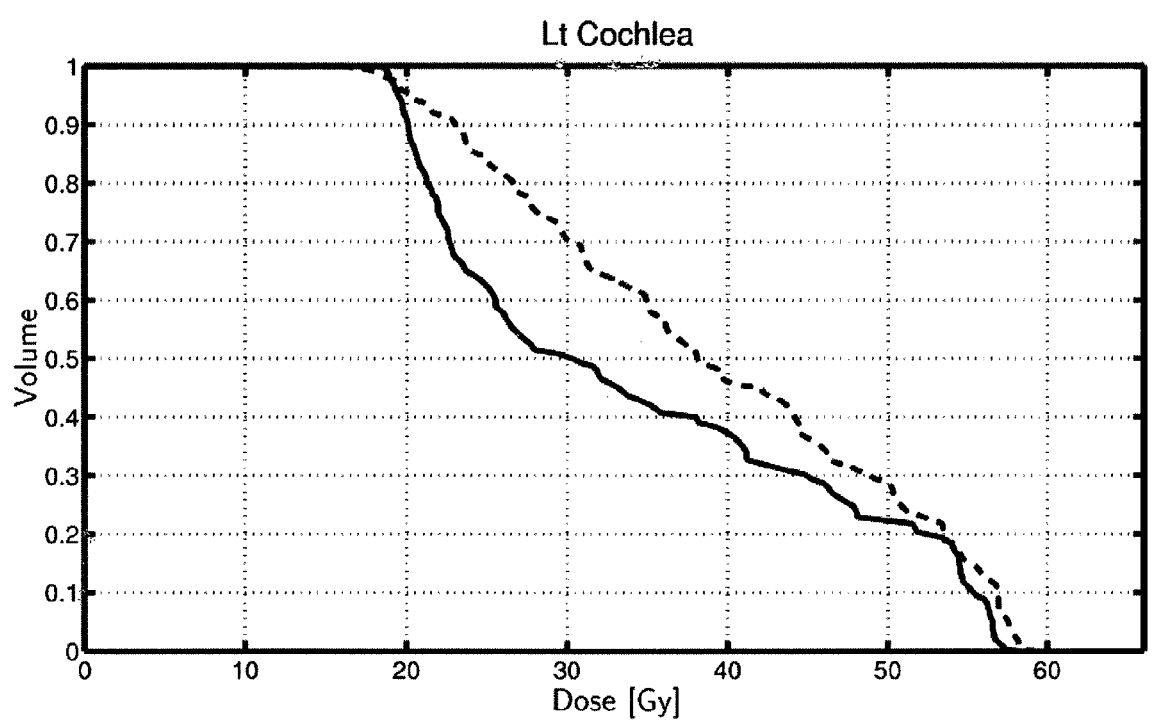
Figure 6F:
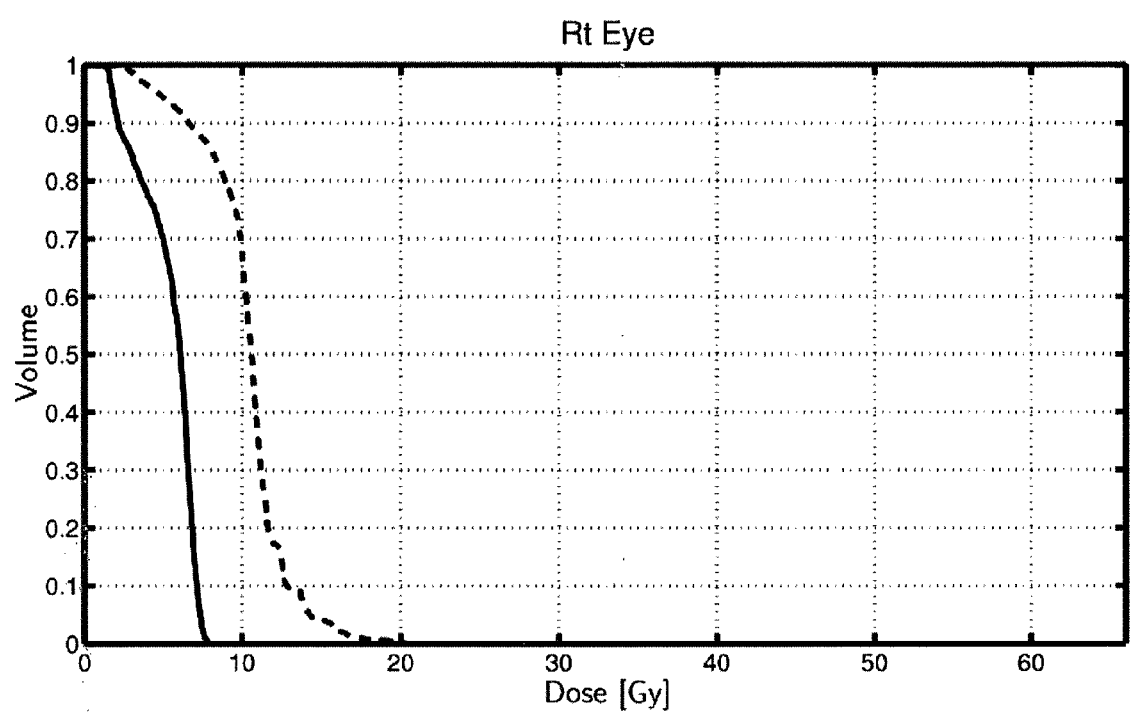
Figure 6G:
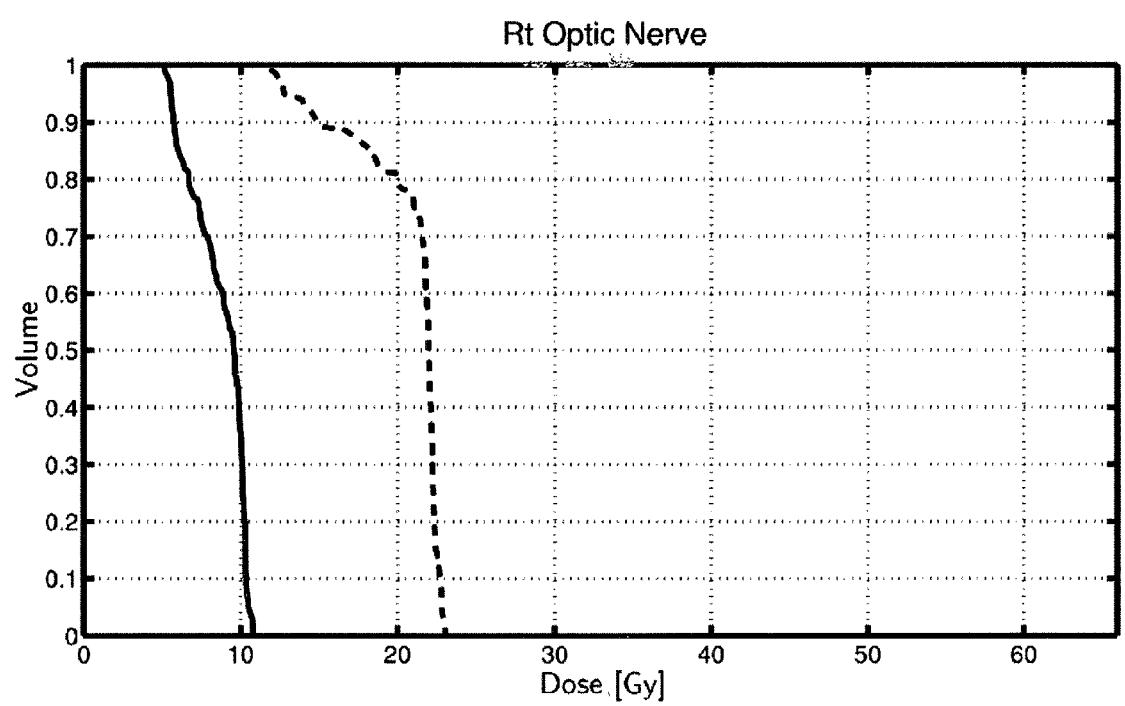
Figure 6H:
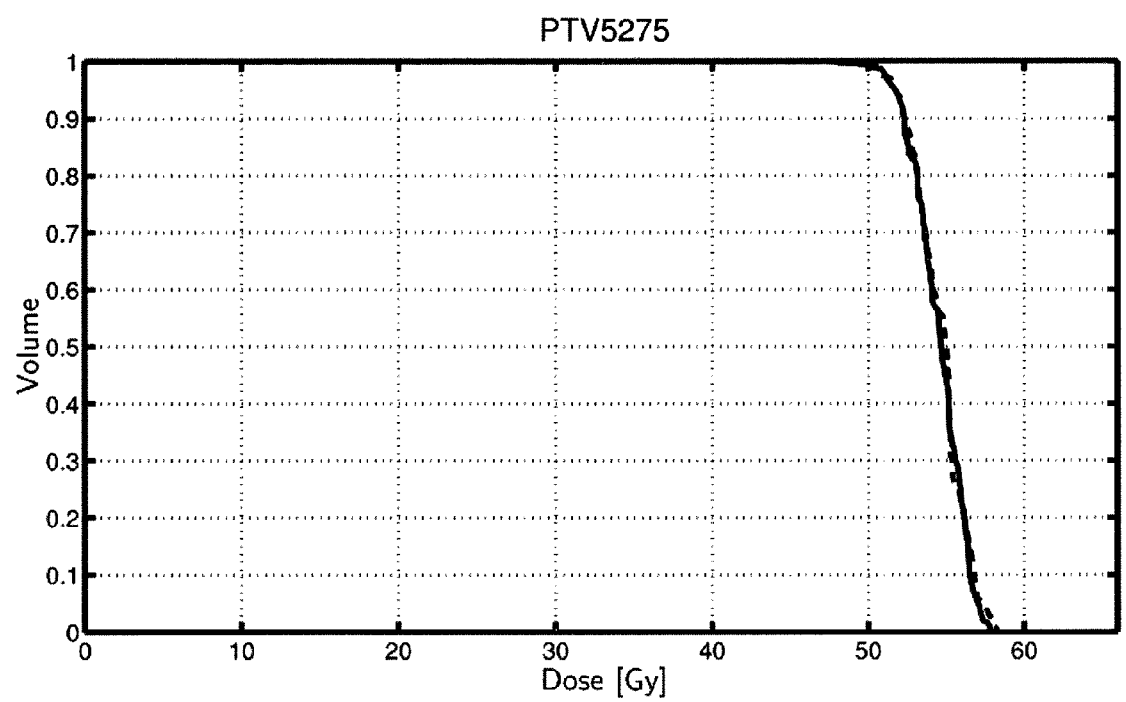
Figure 6I:
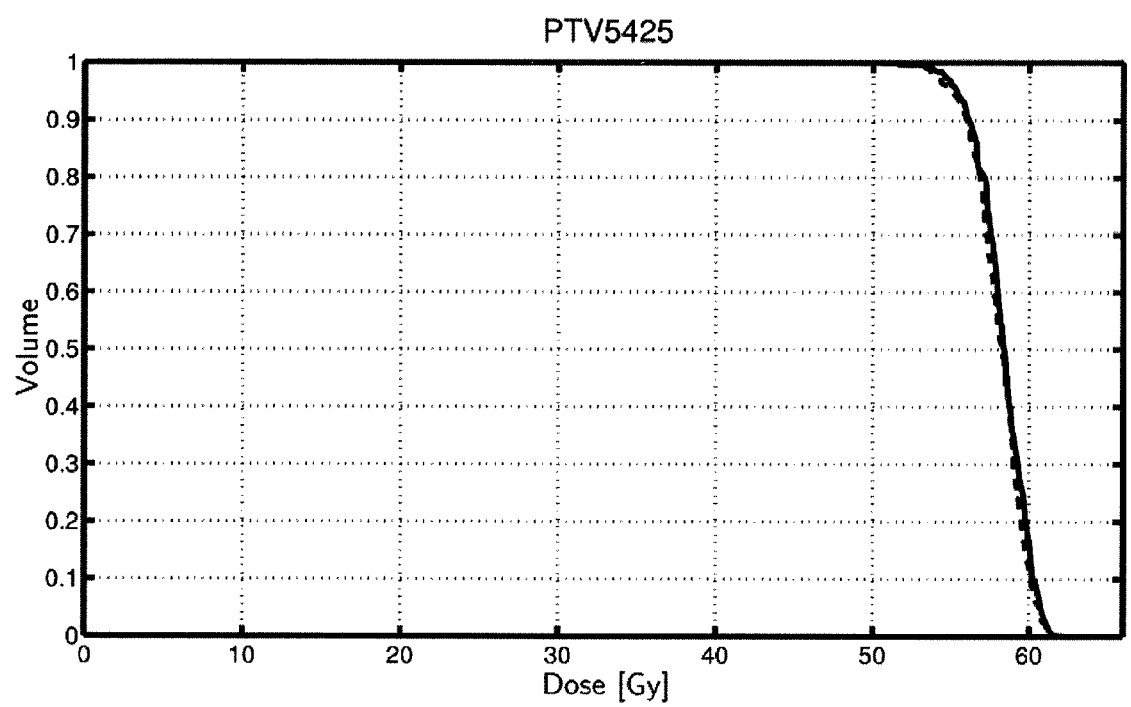
Figure 6J:
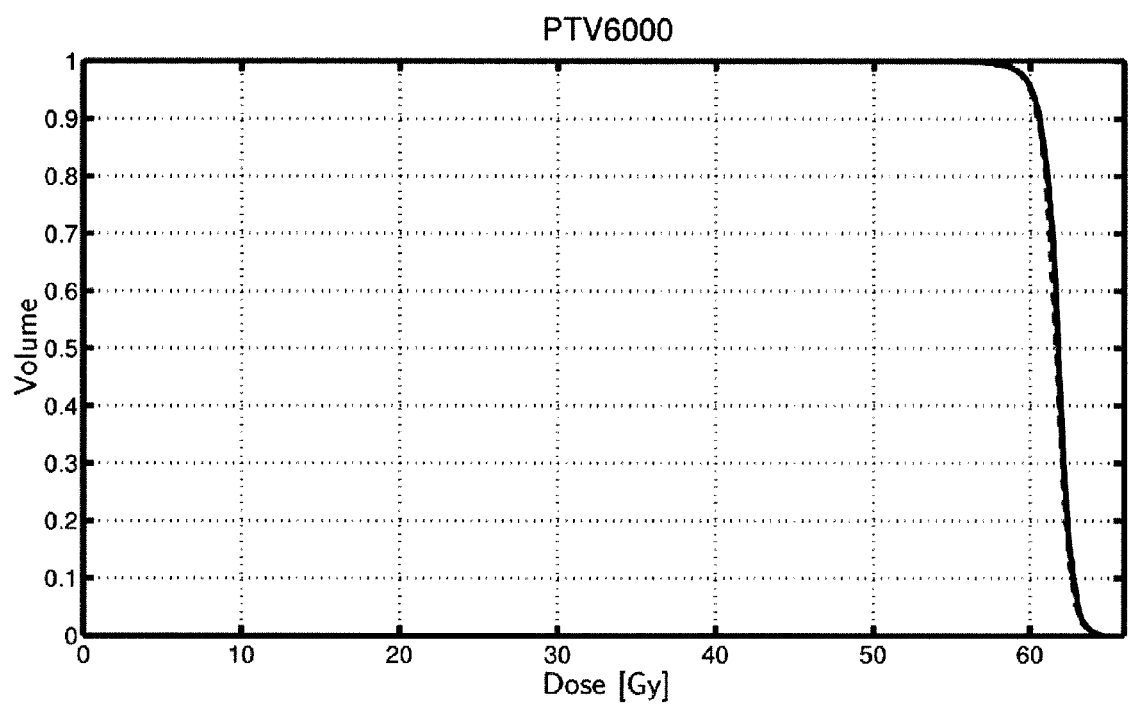

Given a feasible point, a gradient-based optimization algorithm thus has a hard time predicting how large a step can be made to reach a sufficiently optimized solution. The vanishing gradients can be circumvented through regularization of the positive part functions into smooth functions with everywhere nonzero gradients. Therefore, it is proposed to use a smooth and convex regularization of positive part functions, for example by replacing the positive part functions with the log-sum-exp function, as shown in FIG. 5. The proposed log-sum-exp function can be represented by the following equation:

$$lse_\varepsilon(x_1, \ldots, x_n) = \varepsilon \log\left(\sum_{i=1}^n \exp(x_i/\varepsilon)\right) \quad (11)$$

where $\varepsilon > 0$ is a parameter that can be used to determine the exactness of the regularization. As $\varepsilon$ moves towards 0 ($\varepsilon \to 0$), the regularized function converges uniformly to the corresponding positive part function. To avoid overflow, the function can be implemented by the following equation:

$$lse_\varepsilon(x_1, \ldots, x_n) = x_{max} + \varepsilon \log\left(\sum_{i=1}^n \exp((x_i - x_{max})/\varepsilon)\right) \quad (12)$$

with $$x_{max} = \max\{x_i : i = 1, \ldots, n\} \quad (13)$$

For the optimization method, one preferred embodiment is to choose n=2 with one of the exponential terms being exp(0)=1. Therefore, the regularization of the positive part function can be expressed by the following equation:

$$x_+ \approx lse_\varepsilon(x, 0) \quad (14)$$

This approximation satisfies following inequalities:
For $x \in R$ $$x_+ < lse_\varepsilon(x, 0) \leq x_+ + \varepsilon \log 2 \quad (15)$$

FIG. 4 the log-sum-exp function as the regularized positive part function in solid lines, and the positive part function with dashed lines. The maximum error between these functions is attained at x=0. Therefore, when all constraints of the optimization problem expressed by Equations (1)-(4) or expressed by Equations (7)-(10), or a similar problem have been regularized, the corresponding upper bounds must be adjusted to match the errors of the regularizations. For an OAR r that is part of O (r∈O), the regularized constraint corresponding to Equation (2) can be expressed by the following inequality:

$$\sum_{i \in V_r} \Delta v_i^r lse_\varepsilon(d_i(x) - d_i^{ref}, 0) \leq \varepsilon \log 2 \quad (16)$$

For the target ROIs, the constraints can be defined analogously, but the right-hand sides must be modified to correspond to the regularized functions evaluated in the reference dose distribution $d^{ref}$. For a target ROI r that are part of target T (r∈T), the regularized constraints corresponding to Equations (3) and (4) can be expressed by the following inequalities:

$$\sum_{i \in V_r} \Delta v_i^r lse_\varepsilon(\min\{d_i^{ref}, \hat{a}_r\} - d_i(x), 0) \leq \sum_{i \in V_r} \Delta v_i^r lse_\varepsilon(-(d_i^{ref} - \hat{a}_r)_+, 0) \quad (17)$$

$$\sum_{i \in V_r} \Delta v_i^r lse_\varepsilon(d_i(x) - \max\{d_i^{ref}, \hat{a}_r\}, 0) \leq \sum_{i \in V_r} \Delta v_i^r lse_\varepsilon(-(\hat{a}_r - d_i^{ref})_+, 0) \quad (18)$$

When the regularization that is expressed in Equation (14) is applied to the positive part functions of a reference DVH constraint as expressed in Equations (8)-(10), the resulting constraints take the forms as expressed by the following inequalities:

$$\int_0^1 lse_\varepsilon(D_r(v;x) - D_r^{ref}(v), 0) dv \leq \varepsilon \log 2 \quad (19)$$

$$\int_0^1 lse_\varepsilon(\min\{D_r^{ref}(v), \hat{a}_r\} - D_r(v;x), 0) dv \leq \int_0^1 lse_\varepsilon(-(D_r^{ref}(v) - \hat{a}_r)_+, 0) dv \quad (20)$$

$$\int_0^1 lse_\varepsilon(D_r(v;x) - \max\{D_r^{ref}(v), \hat{a}_r\}, 0) dv \leq \int_0^1 lse_\varepsilon(-(\hat{a}_r - D_r^{ref}(v))_+, 0) dv \quad (21)$$

It should be noted that a dose distribution satisfying the regularized constraints does not necessarily satisfy the constraints of the optimization problem expressed by Equations (1)-(4) or expressed by Equations (7)-(10). Since the regularized positive part function is everywhere strictly increasing in the argument, it is possible to remain feasible while delivering higher dose than the reference dose to a voxel provided the dose to another voxel is lower than its reference dose. However, the deficiency must be larger than the excess. One way to reduce the risk of exceeding the reference dose is to separate the voxels of each ROI into a number of subsets, for each of which a constraint is added to the optimization problem. If the voxels of the OAR r that are part of O (r∈O) are separated into subsets $V_r(s)$ for s indexed by $S_r$, the new constraints corresponding to Equation (2) for OAR r take the form of the following inequalities:

$$\sum_{i \in V_r(s)} \Delta v_i^r lse_\varepsilon(d_i(x) - d_i^{ref}, 0) \leq \varepsilon \sum_{i \in V_r(s)} \Delta v_i^r \log 2 \quad (22)$$

$$s \in S_r$$

If the volume of the OAR r that are part of O (r∈O) is split up into subsets $V_r(s)$ for s indexed by $S_r$, the new constraints corresponding to Equation (8) for OAR r take the form of the following inequalities:

$$\int_{v \in V_r(s)}^1 lse_\varepsilon(D_r(v; x) - D_r^{ref}(v), 0) dv \leq \varepsilon \log 2 \int_{v \in V_r(s)} dv \quad (23)$$

$$s \in S_r$$

For the target ROIs that are part of T, analogous equations apply.

This separation into subsets can be performed in a number of ways. For instance, proximate voxels or voxels with reference doses within some given interval may be chosen to belong to the same set. As the separation into subsets is refined, the feasible region of the regularized problem converges to that of the original problem. When the separation is so fine that there is one singleton subset for each voxel, the feasible regions coincide. As in the non-regularized case, it is often advantageous to square the regularized optimization functions or their summands in order to introduce curvature to the problem. In the regularized case, the choice results in optimization problems with different optima because of the nonzero right-hand sides. For many other types of optimization problems, it is not suitable to use the log-sum-exp regularization, since it does not guarantee that accumulated max constraints are satisfied. If it is critical that no constraint is violated, the regularization is thus not advisable. For the IMRT problem that can be optimized by Equations (1)-(4) or (7)-(10), small constraint violations may however be tolerated in some regions, especially when they are compensated by better doses in other regions.

The optimization method of FIG. 2 was evaluated by retrospective planning with a clinical six-field IMRT treatment plan for a brain case as reference plan. The reference plan had been optimized and delivered by a radiation treatment apparatus of a hospital. The log-sum-exp regularization was incorporated with both the reference dose-based optimization functions of Equations (1)-(4) and reference DVH-based optimization functions of Equations (7)-(10) of the RAYSTATION™ treatment planning system version 2.6 of RaySearch Laboratories, serving as the computer system 100. System 100 was then used to perform the dose improvement optimization method. In the dose improvement optimization, the objective was to minimize the sum of the mean doses to each OAR, as expressed by Equation (1). Constraints prevented the DVH of each ROI from becoming worse than in the reference plan. All constraints were regularized using the log-sum-exp regularization, and thus formulated like the Equations (19)-(21) for DVH-based optimization. Each ROI had its constraint split up into two constraints according to Equation (23), with appropriate changes for the target ROIs. The two subsets for each ROI r that is an element of R (r∈R) were selected as the voxels with reference doses in [0, $(D_r^{ref}(0.01) - D_r^{ref}(0.99))/2$) Gy and [$(D_r^{ref}(0.01) - D_r^{ref}(0.99))/2$, ∞) Gy, respectively.

The tumor of the brain case was located in the left hemisphere and enclosed the left eye. The Planning Target Volume (PTV) was divided into three substructures with different dose prescriptions: $PTV_{60}$, $PTV_{54.25}$, and $PTV_{52.75}$, where the subscripts designate the prescribed dose levels in Gy. The ones with lower doses encompassed the left half of the optic chiasm and were used to reduce its dose compared to the dose of $PTV_{60}$. The structures that were included in the optimization were the external ROI, brain, brainstem, expanded optic chiasm, left cochlea, right eye, right optic nerve, the three PTVs, and two ring ROIs surrounding the union of the PTVs, which had been used to improve target conformity.

The optimization algorithm used in the dose improvement optimization was the quasi-Newton sequential quadratic programming algorithm of RayStation, which uses Broyden-Fletcher-Goldfarb-Shanno (BFGS) updates of the approximation of the Hessian of the Lagrangian. However, other types of optimization algorithms are also possible, for example quasi-Newton methods using other update formulae, Newton's method, interior point methods, gradient descent methods, simulated annealing, genetic algorithms, etc. The plan was optimized using direct step-and-shoot optimization. During the optimization, a fast dose computation algorithm based on singular value decomposition of pencil beam kernels was used for dose calculation. Midway into the optimization, accurate dose was calculated using a collapsed cone dose computation algorithm, which was also used to compute final dose for the plan comparisons. The optimization was performed on the dose calculated using the fast algorithm incremental from that of the accurate algorithm.

FIGS. 6A-6J visualize the results of the optimization method according to the present invention, by showing the DVH curves of different volumes resulting from the optimized or improved radiation therapy treatment plan 118 shown in solid lines, as compared with DVH curves of the corresponding volumes of the existing radiation therapy treatment plan 114 that served as a reference plan for the method shown in dashed lines. Generally, the results of the optimization method led to reduced integral dose, reduced mean doses to all organs at risk, and improved target conformity while maintaining target homogeneity. It shows that for the most part, the DVH curves of the OARs are lower in the optimized plan than the DVH curves of the reference plan. Some parts of the reference DVH curves are below the revised curves, namely 8% of the curve for the brain (FIG. 6B), 5% for the expanded optic chiasm (FIG. 6D), 2% for the left cochlea (FIG. 6E), and 1% for the brainstem (FIG. 6C), but in those regions, the difference is very small and not affecting the overall improvement of the existing radiation therapy treatment plan 114. The dose statistics are presented in Table 1 shown below. For each given ROI, $\overline{D}$ denotes the mean dose, $V_x$ denotes the relative volume of the ROI contained by the x Gy isodose volume, and $D_x$ denotes the minimum dose level with an isodose volume containing x % of the ROI The integral dose and all OAR mean doses are reduced in the optimized plan 118.

The target coverage and homogeneity are very similar in the two plans. For $PTV_{60}$, both $D_{98}$ and $D_2$ differ by less than 0.1 Gy between the plans. For $PTV_{54.25}$, and $PTV_{52.75}$ the optimization improved the homogeneity. The dose of the revised plan conforms closer to the target than the dose of the reference plan. This is quantified by a conformity index applied to the union of $PTV_{60}$, $PTV_{54.25}$, and $PTV_{52.75}$, and shown in Table 1 below. The conformity index $CI_{\hat{d}}$ is defined as the ratio between the absolute patient volume receiving higher dose than 95% of the prescribed dose level $\hat{d}$ and the absolute target volume.

TABLE I

| Structure | Statistic | Improved Plan | Reference Plan |
|---|---|---|---|
| External | $\bar{D}$[Gy] | 3.5 | 3.8 |
| Brain | $\bar{D}$[Gy] | 10.6 | 11.8 |
| Brain | $V_{20}$ [%] | 19.3 | 22.1 |
| Brainstem | $\bar{D}$[Gy] | 20.7 | 23.5 |
| Brainstem | $V_{30}$ [%] | 22.7 | 26.3 |
| Expanded optic chiasm | $\bar{D}$[Gy] | 27.5 | 34.1 |
| Expanded optic chiasm | $V_{30}$ [%] | 44.0 | 48.7 |
| Left cochlea | $\bar{D}$[Gy] | 34.6 | 39.3 |
| Left cochlea | $V_{50}$ [%] | 22.3 | 28.9 |
| Right eye | $\bar{D}$[Gy] | 5.4 | 10.3 |
| Right eye | $V_{10}$ [%] | 0.0 | 68.1 |
| Right optic nerve | $\bar{D}$[Gy] | 8.7 | 20.8 |
| Right optic nerve | $V_{20}$ [%] | 0.0 | 79.2 |
| PTV union | $CI_{60}$ [%] | 137.7 | 152.5 |
| PTV union | $CI_{54.25}$ [%] | 182.8 | 197.2 |
| PTV union | $CI_{52.75}$ [%] | 191.4 | 209.0 |
| $PTV_{60}$ | $D_{98}$ [Gy] | 59.3 | 59.3 |
| $PTV_{60}$ | $D_2$ [Gy] | 63.5 | 63.5 |
| $PTV_{54.25}$ | $D_{98}$ [Gy] | 54.5 | 53.9 |
| $PTV_{54.25}$ | $D_2$ [Gy] | 61.2 | 61.1 |
| $PTV_{52.75}$ | $D_{98}$ [Gy] | 51.0 | 50.7 |
| $PTV_{52.75}$ | $D_2$ [Gy] | 57.3 | 57.9 |

The results of Table I show that the existing radiation therapy treatment plan 114 had not been optimized to its full potential and that the proposed method could reduce the doses to all OARs while maintaining target coverage and improving target conformity and homogeneity. The likely cause of this is that the existing radiation therapy treatment plan 114 serving as a reference plan was created using semideviation penalty functions that the optimization algorithm could satisfy in many voxels, leaving no incentive to reduce the OAR doses further, even though it was possible without sacrificing target coverage. Since the objective of the dose improvement optimization is to reduce the mean doses to all healthy structures including the external ROI, it always has an incentive to reduce the dose. It thus avoids ending up at solutions in which all criteria are satisfied even though they could be more strictly enforced. The optimized plan 118 exhibits the structures and volumes where stricter criteria could be introduced in conventional planning for similar cases.

The present invention reduced the total dose to the patient, as shown by the comparison of the external ROI dose in the optimized plan 118 and the existing plan 114. Since the risk of inducing second cancers increases with the total radiation dose, the total dose reduction of the optimized plan 118 shows that the invention can lead to reduced risk of second cancers. That the invention was able to reduce all OAR doses indicates that the method can also reduce the risk of OAR toxicity. For some cases, the present invention could help reducing doses to meet the Radiation Therapy Oncology Group sparing goals.

As can be seen from FIGS. 6B, 6C, 6D and 6E, some but only few volumes of the OARs received higher doses in the optimized plan 118 as compared to the existing plan 114. This is due to the inexactness of the regularization combined with the difference between the fast dose computation algorithm used during the optimization and the accurate dose computation algorithm used to compute final dose. For these volumes, the dose could be reduced by additional intermediate accurate dose calculations and the strategies discussed in above with respect to the regularization of the max-functions, which included increasing the number of constraints and reducing $\epsilon$. Moreover, since the objective favors dose decrements, the regularization is likely of less importance for the OARs than for the target. Reducing $\epsilon$, or dropping the regularization altogether, for the OAR constraints could reduce the likelihood of worse OAR doses in the optimized plan 118 than in the existing plan 114.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A computer-based method for generating an improved radiation therapy treatment plan used for a radiation therapy apparatus for a treatment volume of a body having a target and an organ-at-risk, the method comprising:
   accessing an existing radiation therapy treatment plan for the treatment volume from a memory of a computer, a dose distribution of the existing radiation therapy treatment plan serving as a reference dose distribution, the existing radiation therapy treatment plan being previously created for radiation treatment with the radiation therapy apparatus for the treatment volume of the body of a patient having the target area and the organ-at-risk; and
   performing machine parameter optimization for machine parameters of a radiation therapy apparatus on the existing radiation therapy treatment plan for the treatment volume with the computer and using the dose distribution of the existing radiation therapy treatment plan as the reference dose distribution, by pursuing an optimization goal to minimize doses to volume units of the organ-at-risk by simulating variation of the machine parameters of the radiation therapy apparatus and calculating a direct relationship between the variation of the machine parameters and a variation of the doses to the volume units, thereby generating the improved radiation therapy treatment plan, wherein at least one optimization function relates the reference dose distribution to a dose distribution of the improved radiation therapy treatment plan throughout the machine parameter optimization, wherein the radiation therapy apparatus delivers radiation according to the improved radiation therapy treatment plan.

2. The computer-based method according to claim 1, wherein said pursuing the optimization goal includes:
   minimizing a sum of dose-based functions that evaluate the doses to the volume units as a direct function of the machine parameters that are administered to the organ-at-risk.

3. The computer-based method according to claim 1, wherein said pursuing the optimization goal includes at least one of:

aiming that voxels of the organ-at-risk do not receive a dose that is higher than the reference dose distribution for the organ-at-risk of the existing radiation therapy treatment plan;

aiming that voxels of the target do not receive a dose that is lower than a reference dose of each corresponding voxel of the existing radiation therapy treatment plan, or do not receive a dose that is lower than the prescribed dose to the target; and aiming that voxels of the target do not receive a dose that is higher than a reference dose of each corresponding voxel of the existing radiation therapy treatment plan, or do not receive a dose that is higher than the prescribed dose to the target.

4. The computer-based method according to claim 1, wherein said pursuing the optimization goal includes at least one of:

aiming that a dose-volume-histogram dose of the organ-at-risk is not higher than a corresponding dose of a reference dose-volume-histogram for the organ-at-risk of the existing radiation therapy treatment plan;

aiming that a dose-volume-histogram dose of the target is not lower than a corresponding dose of a reference dose-volume-histogram of the existing radiation therapy treatment plan, or is not lower than the prescribed dose to the target; and aiming that a dose-volume-histogram dose of the target is not higher than a corresponding dose of a reference dose-volume-histogram of the existing radiation therapy treatment plan, or is not higher than the prescribed dose to the target.

5. The computer-based method according to claim 1, further comprising:

displaying a dose-volume histogram for a portion of the organ-at-risk for the existing radiation therapy treatment plan; and displaying a dose-volume histogram for said portion of the organ-at-risk for the improved radiation therapy treatment plan.

6. The computer-based method according to claim 1, wherein said step of performing machine parameter optimization further comprises:

replacing a positive part function used to pursue the optimization goal with a log-sum-exp function having non-zero gradients.

7. The computer-based method according to claim 1, wherein the step of performing machine parameter optimization further comprises:

generating the improved radiation therapy treatment plan that reduces the integral dose of the existing radiation therapy treatment plan.

8. A computer system for generating an improved radiation therapy treatment plan used for a radiation therapy apparatus for a treatment volume of a body having a target and an organ-at-risk, the system comprising:

a storage device for storing an existing radiation therapy treatment plan for the treatment volume, a dose distribution of the existing radiation therapy treatment plan serving as a reference dose distribution, the existing radiation therapy treatment plan being previously created for radiation treatment with the radiation therapy apparatus for the treatment volume of the body of a patient having the target area and the organ-at-risk; and a hardware processor for performing machine parameter optimization for parameters of the radiation therapy apparatus on the existing radiation therapy treatment plan for the treatment volume and using the dose distribution of the existing radiation therapy treatment plan as the reference dose distribution by pursuing an optimization goal to minimize doses to volume units of the organ-at-risk by simulating a variation of the machine parameters of the radiation therapy apparatus and calculating a direct relationship between the variation of the machine parameters and a variation of the doses to the volume units, thereby generating the improved radiation therapy treatment plan, wherein at least one optimization function relates the reference dose distribution to a dose distribution of the improved radiation therapy treatment plan throughout the machine parameter optimization, wherein the radiation therapy apparatus delivers radiation according to the improved radiation therapy treatment plan.

9. The computer system according to claim 8, wherein said pursuing the optimization goal includes:

minimizing a sum of dose-based functions that evaluate the doses to the volume units as a direct function of the machine parameters that are administered to the organ-at-risk.

10. The computer system according to claim 8, wherein said pursuing the optimization goal includes at least one of:

aiming that voxels of the organ-at-risk do not receive a dose that is higher than the reference dose distribution for the organ-at-risk of the existing radiation therapy treatment plan;

aiming that voxels of the target do not receive a dose that is lower than a reference dose of each corresponding voxel of the existing radiation therapy treatment plan, or do not receive a dose that is lower than the prescribed dose to the target; and aiming that voxels of the target do not receive a dose that is higher than a reference dose of each corresponding voxel of the existing radiation therapy treatment plan, or do not receive a dose that is higher than the prescribed dose to the target.

11. The computer system according to claim 8, wherein said pursuing the optimization goal includes at least one of:

aiming that a dose-volume-histogram dose of the organ-at-risk is not higher than a corresponding dose of a reference dose-volume-histogram for the organ-at-risk of the existing radiation therapy treatment plan;

aiming that a dose-volume-histogram dose of the target is not lower than a corresponding dose of a reference dose-volume-histogram of the existing radiation therapy treatment plan, or is not lower than the prescribed dose to the target; and aiming that a dose-volume-histogram dose of the target is not higher than a corresponding dose of a reference dose-volume-histogram of the existing radiation therapy treatment plan, or is not higher than the prescribed dose to the target.

12. The computer system according to claim 8, further comprising:

a display device for displaying a dose-volume histogram for a portion of the organ-at-risk for the existing radiation therapy treatment plan, and for displaying a dose-volume histogram for said portion of the organ-at-risk for the improved radiation therapy treatment plan.

13. The computer system according to claim 8, wherein the hardware processor that performs machine parameter optimization further replaces a positive part function used to pursue the optimization goal with a log-sum-exp function having non-zero gradients.

14. The computer system according to claim 8, wherein the hardware processor that performs machine parameter optimization further generates the improved radiation therapy treatment plan by reducing the integral dose of the existing radiation therapy treatment plan.

15. A non-transitory computer readable medium having computer instructions recorded thereon, the computer instructions configured to perform a method for generating an improved radiation therapy treatment plan used for a radiation therapy apparatus for a treatment volume having a target and an organ-at-risk when executed on a computer, the method comprising the steps of:
  accessing an existing radiation therapy treatment plan for the treatment volume from a memory of a computer, a dose distribution of the existing radiation therapy treatment plan serving as a reference dose distribution, the existing radiation therapy treatment plan being previously created for radiation treatment with the radiation therapy apparatus for the treatment volume of the body of a patient having the target area and the organ-at-risk; and
  performing machine parameter optimization for machine parameters of the radiation therapy apparatus on the existing radiation therapy treatment plan with the computer and using the dose distribution of the existing radiation therapy treatment plan for the treatment volume as the reference dose distribution, by pursuing an optimization goal to minimize doses to volume units the organ-at-risk by simulating a variation of the machine parameters of the radiation therapy apparatus and calculating a direct relationship between the variation of the machine parameters and a variation of the doses to the volume units, thereby generating the improved radiation therapy treatment plan,
  wherein at least one optimization function relates the reference dose distribution to a dose distribution of the improved radiation therapy treatment plan throughout the machine parameter optimization, wherein the radiation therapy apparatus delivers radiation according to the improved radiation therapy treatment plan.

16. The non-transitory computer readable medium according to claim 15, wherein said pursuing the optimization goal includes:
  minimizing a sum of dose-based functions that evaluate the doses to the volume units as a direct function of the machine parameters that are administered to the organ-at-risk.

17. The non-transitory computer readable medium according to claim 15, wherein said pursuing the optimization goal includes at least one of:
  aiming that voxels of the organ-at-risk do not receive a dose that is higher than the reference dose distribution for the organ-at-risk of the existing radiation therapy treatment plan;
  aiming that voxels of the target do not receive a dose that is lower than a reference dose of each corresponding voxel of the existing radiation therapy treatment plan, or do not receive a dose that is lower than the prescribed dose to the target; and
  aiming that voxels of the target do not receive a dose that is higher than a reference dose of each corresponding voxel of the existing radiation therapy treatment plan, or do not receive a dose that is higher than the prescribed dose to the target.

18. The non-transitory computer readable medium according to claim 15, wherein said pursuing the optimization goal includes at least one of:
  aiming that a dose-volume-histogram dose of the organ-at-risk is not higher than a corresponding dose of a reference dose-volume-histogram for the organ-at-risk of the existing radiation therapy treatment plan;
  aiming that a dose-volume-histogram dose of the target is not lower than a corresponding dose of a reference dose-volume-histogram of the existing radiation therapy treatment plan, or is not lower than the prescribed dose to the target; and
  aiming that a dose-volume-histogram dose of the target is not higher than a corresponding dose of a reference dose-volume-histogram of the existing radiation therapy treatment plan, or is not higher than the prescribed dose to the target.

19. The non-transitory computer readable medium according to claim 15, said method further comprising:
  displaying a dose-volume histogram for a portion of the organ-at-risk for the existing radiation therapy treatment plan; and
  displaying a dose-volume histogram for said portion of the organ-at-risk for the improved radiation therapy treatment plan.

20. The non-transitory computer readable medium according to claim 15, wherein said step of performing machine parameter optimization further comprises:
  replacing a positive part function used to pursue the optimization goal with a log-sum-exp function having non-zero gradients.

21. The non-transitory computer readable medium according to claim 15, wherein the step of performing machine parameter optimization further comprises:
  generating the improved radiation therapy treatment plan that reduces the integral dose of the existing radiation therapy treatment plan.

22. The computer-based method according to claim 1, wherein the machine parameters include at least one of bixel weights, spot weights, multi-leaf collimator leaf positions, jaw positions, segment weights, monitor units, collimator angles, couch angles, gantry angles, wedge angles, and arc delivery times.

23. The computer system according to claim 8, wherein the machine parameters include at least one of bixel weights, spot weights, multi-leaf collimator leaf positions, jaw positions, segment weights, monitor units, collimator angles, couch angles, gantry angles, wedge angles, and arc delivery times.

24. The non-transitory computer readable medium according to claim 15, wherein the machine parameters include at least one of bixel weights, spot weights, multi-leaf collimator leaf positions, jaw positions, segment weights, monitor units, collimator angles, couch angles, gantry angles, wedge angles, and arc delivery times.

25. The computer-based method according to claim 1, wherein said pursuing the optimization goal includes:
  minimizing a sum of dose-based functions that evaluate the doses to the volume units with a non-linear direct relationship to the machine parameters that are administered to the organ-at-risk.

26. The computer system according to claim 8, wherein said pursuing the optimization goal includes:
  minimizing a sum of dose-based functions that evaluate the doses to the volume units with a non-linear direct relationship to the machine parameters that are administered to the organ-at-risk.

27. The non-transitory computer readable medium according to claim 15, wherein said pursuing the optimization goal includes:

minimizing a sum of dose-based functions that evaluate the doses to the volume units with a non-linear direct relationship to the machine parameters that are administered to the organ-at-risk.

* * * * *